United States Patent [19]

Lagny et al.

[11] Patent Number: 5,798,391
[45] Date of Patent: Aug. 25, 1998

[54] INJECTABLE SOLUTION OF BENZALKONIUM FLUORIDE

[75] Inventors: Pierre Lagny, Kildare, Ireland; Pierre Bourbon, Toulouse, France

[73] Assignee: Aromafarm Limited, Isle of Man, United Kingdom

[21] Appl. No.: 682,500

[22] PCT Filed: Jan. 23, 1995

[86] PCT No.: PCT/FR95/00070

§ 371 Date: Oct. 22, 1996

§ 102(e) Date: Oct. 22, 1996

[87] PCT Pub. No.: WO95/19766

PCT Pub. Date: Jul. 27, 1995

[30] Foreign Application Priority Data

Jan. 24, 1994 [FR] France ................... 94 00695

[51] Int. Cl.[6] .................................. A61K 31/14
[52] U.S. Cl. .................. 514/643; 514/885; 514/924
[58] Field of Search ................... 514/643, 885, 514/924

[56] References Cited

U.S. PATENT DOCUMENTS 5,026,561  6/1991  Bourbon et al. ................... 424/673

FOREIGN PATENT DOCUMENTS 0 046 594  3/1982  European Pat. Off. .
0 308 564  3/1989  European Pat. Off. .

*Primary Examiner*—Kimberly Jordan
*Attorney, Agent, or Firm*—Young & Thompson

[57] ABSTRACT

Solution administrable by intravascular injection in a human or an animal which comprises an effective amount up to 0.23% by weight of a benzalkonium fluoride having the formula:

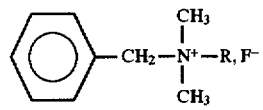

where R is an alkyl radical which may vary between $C_8H_{17}$ and $C_{18}H_{37}$, dissolved in an excipient injectable intravascularly. Preferably R is between $C_{12}H_{25}$ and $C_{14}H_{29}$, and more preferably $C_{14}H_{29}$. The solution can be packaged in 10 ml ampoules, containing about 21 mg of benzalkonium fluoride, the benzalkonium fluoride being dissolved in a physiological solvent. The solution also contains at least one metallic derivative of fluorine, preferably lithium fluoride.

23 Claims, 4 Drawing Sheets

INJECTABLE SOLUTION OF BENZALKONIUM FLUORIDE

This application is a 371 of PCT/FR95/00070, filed Jan. 23, 1995.

The invention concerns a solution which can be administered intravascularly consisting of at least one benzalkonium fluoride.

EP-A-0.308,564 already mentions the use of benzalkonium fluoride to obtain a composition for general or parenteral administration with between 0.05% and 7%, more particularly of the order of 1% in weight of benzalkonium fluoride, intented to act against viruses and retroviruses, particularly herpes or the LVAs responsible for AIDS.

Nevertheless, benzalkonium fluoride is supposed, as with all the benzalkonium salts which are tensio-active, to have a strong hæmolytic effect, prohibiting its intravascular administration. Thus, although general or parenteral administration of benzalkonium fluoride are mentionned in EP-A-0.308,564, its use in practice comes up against this difficulty, until now considered insurmountable for two reasons: the concentration to reach in the blood to arrive at an activity was itself supposed to lead to hæmolysis of the blood; injection, even administered very slowly, supposes the local creation of a high, thus hæmolytic, concentration of benzalkonium fluoride. In particular, injection of this salt at concentrations of the order of 1% weight appeared to be impossible. Now this concentration was considered indispensable to obtain a sufficient activity. We thus renounced the use of benzalkonium salts, and particularly benzalkonium fluoride, by intravascular administration, considering that the concentrations of the injected solutions would suppress all virucidal and bactericidal activity, taking into account the minimal inhibiting concentration measured in vitro, and that, even at these low concentrations, a very high risk of hæmolysis, and thus immediate death, persists. Thus until now, intravascular administration of benzalkonium salts, and notably benzalkonium fluoride in man or animals was considered purely and simply forbidden.

A constant need makes itself felt for a shock treatment against viral or infectious affections, notably of immunodeficient origin, and in particular in the treatment of patients suffering from AIDS in the declared or evolutive phase which present severe opportunistic infections leading rapidly to dehydration and death.

Such a shock treatment poses a series of apparently contradictory problems, however:
- it should act not only against the pathogenic microorganisms responsible for the deteriorated clinical state of the patient, but equally against the virus responsible for the immunodeficiency (the case of AIDS),
- it should have a very wide action spectrum, taking into account the great variety of affections which may be involved in the case of an immunodeficiency,
- it should nevertheless be free of side effects, and in particular should not irritate or attack healthy organs or cells in an already considerably weakened organism.

The invention thus aims in a general way at finding a solution to this general problem which has not, until now, been resolved. It thus aims at offering a treatment to patients suffering from viral or severe infectious affections, particularly multiple ones, such as those due to an immunodeficiency.

More particularly, the inventors discovered with surprise that, among the quaternary ammoniums, benzalkonium fluoride can be effectively injected intravascularly without risk of hæmolysis within a precise range of concentrations with which an effective activity is, nevertheless, noted.

The invention thus aims more particularly at offering an injectable solution of an antiviral or anti-infectious agent such as a benzalkonium salt.

For this, the invention concerns a solution administerable intravascularly, characterised by a content of the order of 0.23% or less in weight of a benzalkonium fluoride having the formula:

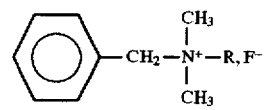

where R is an alkyl radical which may vary between $C_8H_{17}$ and $C_{18}H_{37}$, dissolved in an excipient injectable intravascularly.

We could in effect note that when the proportions by weight of benzalkonium fluoride are of the order of 0.23% or less, and more particularly of the order of 0.20% of weight, no hæmolysis is to be feared in general, contrary to the previous general opinion of the art. Also, a clinical improvement can be noted in using concentrations greater than 0.05% of weight of benzalkonium fluoride. Thus the solution according to the invention is between 0.05 and 2.3 g/l—more particularly of the order of 2.1 g/l—of benzalkonium fluoride, preferably a benzalkonium fluoride in which R is $C_{14}H_{29}$.

More particularly, the solution according to the invention consists of a concentration of benzalkonium fluoride determined to permit administration by slow injection of unit doses of the order of 0.5 to 23 mg—notably of the order of 21 mg—of benzalkonium fluoride per liter of blood of the patient to be treated. Thus, in the case of a man having five liters of blood, we prepare an injected dose of 2.5 to 130 mg, more particularly of the order of 105 mg, of benzalkonium fluoride.

Thus, according to the invention, two conditions should be brought together to allow intravascular injection of benzalkonium fluoride: the concentration of benzalkonium fluoride in the injected solution should be less than 0.23% and the total quantity injected per liter of blood of the patient should remain inferior to 23 mg.

To determine the concentration of benzalkonium fluoride in the solution to be injected, we take a blood sample from the patient immediately before injection, submit this blood to in vitro hæmolytic tests with a solution consisting initially of 0.23% of benzalkonium fluoride, and reduce the concentrations until a non-hæmolytic solution is obtained.

According to the invention, before injection we verify the non hæmolytic character of the solution by determining the hæmolytic concentration on the patient's blood.

The solution according to the invention may be packaged in ampoules from 5 to 15 ml—more particularly 10 ml—consisting of between 0.5 and 23 mg—more particularly 21 mg for a 10 ml ampoule—of benzalkonium fluoride respecting the maximum value of 0.23%. And we inject between 5 and 15 ml, more particularly 10 ml, of the solution per litre of blood, more particularly 50 ml in the case of a man.

The solution according to the invention advantageously consists of benzalkonium fluoride dissolved in a physiological solute. R falls advantageously between $C_{12}H_{25}$ and $C_{14}H_{29}$. According to the invention, the solution may contain, among others, at least a metallic fluorine derivative, and more particularly lithium fluoride.

The invention further relates to the application of at least a benzalkonium fluoride whose formula is given above, dissolved in a concentration of the order of or less than 0.23% of weight in an excipient injectable intravascularly for combatting viral or infectious disease, notably of an immunodeficient origin. More particularly, the invention concerns at least such a benzalkonium fluoride dissolved at a concentration of the order or less than 0.23% of weight in an excipient injectable intravascularly to obtain a solution administerable intravascularly for combatting AIDS in the declared or evolutive phase. The invention thus relates to a method of treating viral or infectious diseases, notably of an immunodeficient origin, such as AIDS in the declared or evolutive phase in which we inject a solution according to the invention intravascularly. In the method of the invention, we inject a solution after having determined ex vivo the hæmolytic potential of benzalkonium fluoride vis-a-vis the patient's blood, the solution injected having a concentration inferior to this hæmolytic concentration, and we administer by slow injection a quantity of benzalkonium fluoride between 0.5 and 23 mg per litre of blood of the patient to be treated, more particularly and preferably between 20 and 23 mg.

Thus, in an application according to the invention, we use between 0.5 and 23 mg—more particularly of the order of 21 mg—of benzalkonium fluoride dissolved in 10 ml of solute.

The invention is therefore particularly useful in the treatment of viral diseases which destroy the immune defences, and more particularly as a shock treatment. The invention has thus permitted effective treatment of cases of Carré's disease and cases of AIDS in an advanced phase, that is developing opportunistic infectious diseases.

Other characteristics and advantages of the invention will appear in the examples given below.

IN VITRO VIRUCIDE TRIALS

Example 1

Figure 1:
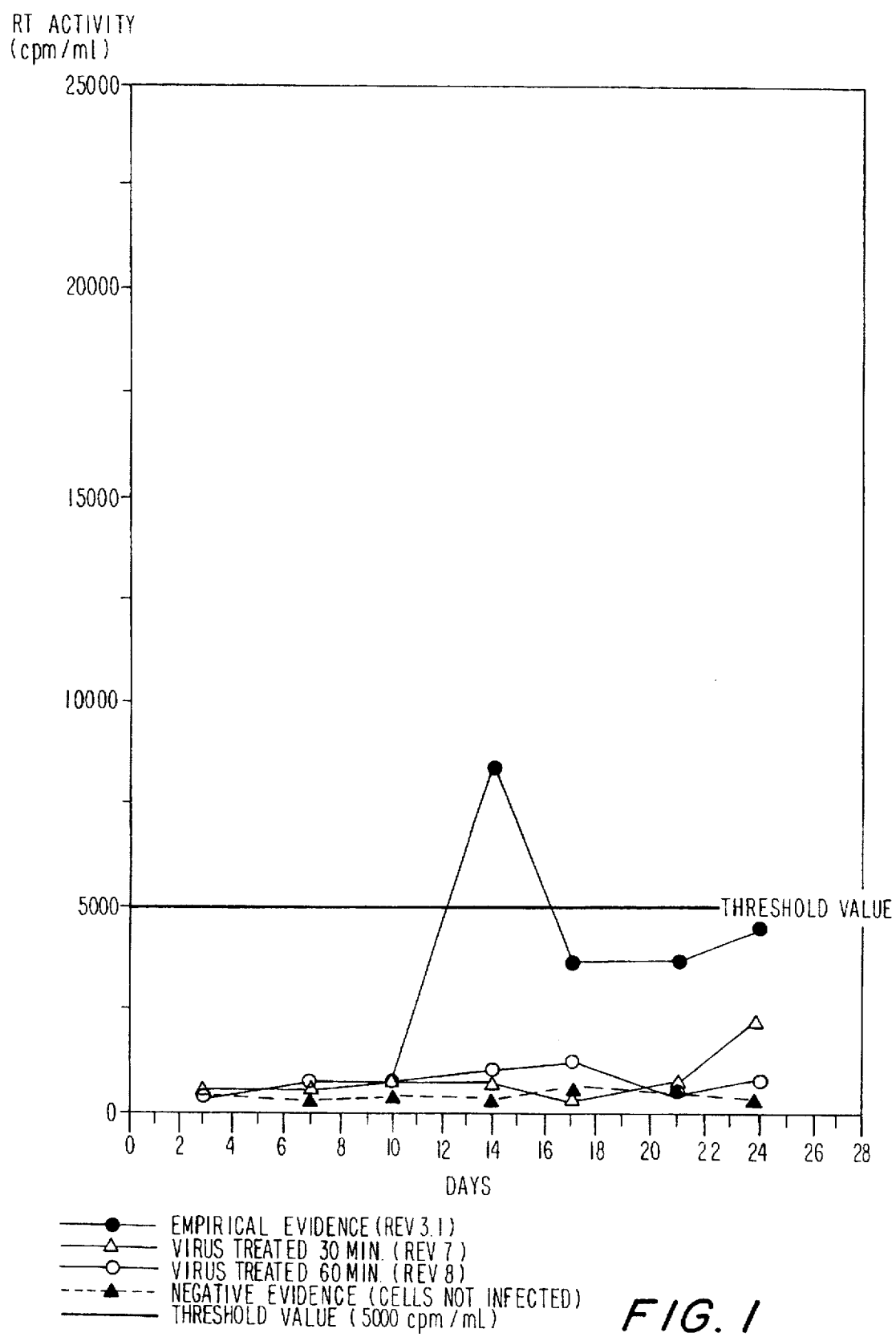
FIGS. 1 to 4 given as appendices represent curves resulting from in vitro measurement tests of virucide activity of on the HIV-1 virus of benzalkonium fluoride conforming to example 2 described below.

We have determined the virucide activity of tetradecyl-dimethyl-benzyl-ammonium fluoride (BKF) vis-a-vis vertebrate viruses in conformance with French Standard AFNOR T72-180, December 1989. This benzalkonium fluoride was diluted in solution in sterile distilled water at the following concentrations: 0.02, 0.01, 0.005% (weight divided by volume).

The tests were carried out on the following viral strains:
picornaviridæ: polio enerovirus 1, SABIN strain, cultivated on VERO cell, adenoviridæ: adenovirus type 5, cultivated on KB cell, herpetoviridæ: Herpes Simplex Virus Type 1 (HSV 1) and Herpes Simplex Virus Type 2 (HSV 2) supplied by the Institut Pasteur and cultivated on cell MCR-5.

The water, the culture medium and the reagents are those recognised by Standard AFNOR T72-180. The titration of the virus is by reading the cytopathic test, following the method described in Standard AFNOR T72-180. The calculation of the infectious titration is by the FISHER and YATES method with the WYSHAK and DETRE tables. The results are given in number of infectious units per ml, or plaque-forming units per ml (PFU/ml).

We first sought the toxicity threshold (D.L.0) of benzalkonium fluoride. Before filtration, this toxicity threshold was 0.05% (in mg per ml). After filtration, the toxicity threshold was 0.01%.

The capacity of cells treated with benzalkonium fluoride to develop the viral infection was determined and the results a given in Table 1.

TABLE 1

CAPACITY OF CELLS TREATED BY BKF
TO DEVELOP THE VIRAL INFECTION
Titration of viral suspensions (PFU/ml)

| Strains | Control | After contact with benzaikonium fluoride |
|---|---|---|
| ENTEROVIRUS POLIO 2 | $10^{7.68}$ | $10^{6.98}$ |
| ADENOVIRUS Type 5 | $10^{8.64}$ | $10^{7.56}$ |
| HERPES SIMPLEX VIRUS Type 2 (HSV 2) | $10^{8.00}$ | $10^{7.02}$ |
| HERPES SIMPLEX VIRUS Type 2 (HSV 2) | $10^{8.50}$ | $10^{7.84}$ |

The virucidal activity was then determined by the technique known as molecular screening, consisting of filtration on sephadex gel LH 20 and using subcytotoxic concentrations of benzalkonium fluoride. The virucidal activity was determined as a function of contact time between the benzalkonium fluoride and the viral strain. Different samples were taken at predetermined time intervals, submitted to a centrifugation for 8 minutes at 1,000 g, then titrated on microplates. A control viral suspension without benzalkonium fluoride was treated following the same methodology. Tables 2 to 5 give the results obtained in kinetic terms of the inactivation of the virus as a function of contact time with the benzalkonium fluoride and its concentration. The virucidal activity of benzalkonium fluoride (BKF) is determined by the minimal concentration and minimal contact time with the virus which provoked a reduction of infectious titration of the viruses by a logarithmic factor of a least 4. The tests were carried out at 32° C.

TABLE 2

VIRUCIDAL ACTIVITY OF BKF ON ENTEROVIRUS POLIO 1
Viral Titration (PFU/ml)

| Concentration of BKF | Virus/BKF contact time (minutes) | | | |
|---|---|---|---|---|
| (%) (m/V) | 15 | 30 | 60 | 120 |
| 0.02 | $10^{3.28}$ | $10^{2.02}$ | $10^{1.40}$ | 0 |
| 0.01 | $10^{1.28}$ | 0 | 0 | 0 |
| 0.005 | $10^{4.38}$ | $10^{3.62}$ | $10^{3.02}$ | $10^{2.26}$ |

TABLE 3

VIRUCIDAL ACTIVITY OF BKF ON ADENOVIRUS TYPE 5
Viral Titration (PFU/ml)

| Concentration of BKF | Virus/BKF contact time (minutes) | | | |
|---|---|---|---|---|
| (%) (m/V) | 15 | 30 | 60 | 120 |
| 0.02 | $10^{5.88}$ | $10^{5.02}$ | $10^{4.16}$ | $10^{2.68}$ |
| 0.01 | $10^{5.04}$ | $10^{4.38}$ | $10^{3.86}$ | $10^{3.02}$ |
| 0.005 | $10^{6.00}$ | $10^{5.65}$ | $10^{5.10}$ | $10^{4.60}$ |

TABLE 4

VIRUCIDAL ACTIVITY OF BKF ON HERPES SIMPLEX
VIRUS TYPE 1
Viral Titration (PFU/ml)

| Concentration of BKF | Virus/BKF contact time (minutes) | | | |
|---|---|---|---|---|
| (%) (m/V) | 15 | 30 | 60 | 120 |
| 0.02 | 0 | 0 | 0 | 0 |
| 0.01 | $10^{1.68}$ | 0 | 0 | 0 |
| 0.005 | $10^{4.26}$ | $10^{3.15}$ | $10^{2.27}$ | $10^{1.36}$ |

TABLE 5

VIRUCIDAL ACTIVITY OF BKF ON HERPES SIMPLEX
VIRUS TYPE 2
Viral Titration (PFU/ml)

| Concentration of BKF | Virus/BKF contact time (minutes) | | | |
|---|---|---|---|---|
| (%) (m/V) | 15 | 30 | 60 | 120 |
| 0.02 | 0 | 0 | 0 | 0 |
| 0.01 | $10^{2.68}$ | $10^{1.41}$ | 0 | 0 |
| 0.005 | $10^{8.14}$ | $10^{4.65}$ | $10^{3.84}$ | $10^{2.26}$ |

These tests thus confirmed the virucidal activity of benzalkonium fluoride at the following concentrations (m/V) and contact times: 0.01% in 30 minutes on Polio 1 enterovirus; 0.02% in 120 minutes on Type 5 adenovirus; 0.01% in 5 minutes on Herpes Simplex Virus Type 1; 0.01% in 15 minutes on Herpes Simplex Virus Type 2 at 32° C. following Standard AFNOR T72-180.

Example 2

The virucidal activity of benzalkonium fluoride was tested on the HIV-1 virus (LAI strain) responsible for AIDS by the Institut Pasteur using the infectiousness test on primary culture of activated human lymphocytes test.

The study was carried out in two steps: we first treated the virus with a solution of benzalkonium fluoride (BKF) at 20 μg/ml, then we studied the residual infectiousness of the treated virus on a primary culture of activated human lymphocytes.

For treatment of the virus, the contact time at room temperature was 30 minutes and 60 minutes, 0.9 ml of the virus added to 100 μl of BKF was left for 30 minutes at room temperature, then diluted in 10 ml of NTE buffer. The sample obtained is referenced REV7. Sample REV8 corresponds to 0.9 ml of the virus added to 100 μl of BKF left for 60 minutes at room temperature then diluted in 10 ml of NTE buffer. After dilution in the buffer, the samples were centrifuged for 35 minutes at 40,000 rev/min in order to eliminate the product possibly toxic for the infectiousness test cells, and to concentrate the residual infectious virus. After centrifuging, the residue was resuspended in 1 ml of culture medium, sealed and stored at −80° C.

Samples REV1, REV2 and REV3.1 were the positive controls for the experiment, REV1 corresponding to 0.9 ml of viral suspension frozen at −80° C., REV2 corresponding to 0.9 ml of viral suspension diluted and centrifuged in the same way as samples REV7 and REV8 in order to evaluate the loss of infectiousness during the centrifuging stage. REV3.1 corresponded to 0.9 ml of viral suspension left at room temperature for 60 minutes (maximum duration of the study) then diluted in NTE buffer and centrifuged in the same way as the treated samples, in order to evaluate the loss of infectiousness due to the experimental conditions used for BKF.

A sample, REV4, of 1 ml of BKF at 20 μg/ml diluted in 10 ml of NTE buffer and centrifuged under the conditions described for the treated virus, was used to control any possible toxicity on the infectiousness test cells due to traces of residual product not eliminated during centrifuging. This sample was thus used as negative control with the non-infected infectiousness test cells.

The tests in the real sense consisted in searching for the residual infectious power of the treated virus on activated human PBMC lymphocytes. To do so, the lymphocytes, which were previously stimulated, were incubated with 1 ml of each virus sample, treated or not, diluted by 10 in 10 (from $10^{-4}$ to $10^{-7}$ for the negative controls and from $10^{-1}$ to $10^{-5}$ for the samples of treated virus). The cells were centrifuged and resuspended at $10^6$ cells per ml in a complete medium. Every three or four days, the cells were counted, reseeded and the supernatants stored at −80° C. After analysis of the results, a second experiment was carried out in an identical way, inoculating the cells with half dilutions of the samples of virus treated with BKF.

Next, we measured the activity of reverse transcriptase (RT) in the supernatants of the cell cultures. The supernatants saved on each cellular passage (days n° 3, 7, 10, 14, 17, 21, 24 for the first experiment and 3, 6, 9, 13, 16, and 20 for the second experiment) were tested and their reverse transcriptase activity was quantified after concentration by ultra-centrifuging.

We also quantified the HIV-1 antigen P25 using the Elisa "Sandwich" technique on the same supernatants culture on days n° 3, 10, 17 and 24 for the first experiment and 3, 9, 16 and 20 for the second experiment after inoculation of the cells. The ELAVIA Ag1 kit available from the Société Diagnostics Pasteur was used. We noted that control samples REV4 were not toxic for the infectiousness test cells.

Table 6 gives the results obtained for reverse transcriptase activity with the control samples.

TABLE 6

VIRUCIDE ACTIVITY TEST OF KBF
ON PRIMARY CULTURE OF ACTIVATED HUMAN LYMPHOCYTES
TITRATION IN DILUTION OF CONTROL VIRAL SAMPLES

| Sample | Dilution | RT activity at different days (cpm/ml*) | | | | | | |
|---|---|---|---|---|---|---|---|---|
| | | Day 3 | Day 7 | Day 10 | Day 14 | Day 17 | Day 21 | Day 24 |
| REV1 | $10^{-4}$ | 391 | 4,304 | 26,311 | 47,192 | 5,529 | 888 | 712 |
| control | $10^{-5}$ | 1,354 | 1,786 | 5,417 | 36,738 | 8,450 | 7,157 | 3,854 |

TABLE 6-continued

VIRUCIDE ACTIVITY TEST OF KBF
ON PRIMARY CULTURE OF ACTIVATED HUMAN LYMPHOCYTES
TITRATION IN DILUTION OF CONTROL VIRAL SAMPLES

| | | RT activity at different days (cpm/ml*) | | | | | | |
|---|---|---|---|---|---|---|---|---|
| Sample | Dilution | Day 3 | Day 7 | Day 10 | Day 14 | Day 17 | Day 21 | Day 24 |
| positive | $10^{-6}$ | 335 | 652 | 2,459 | 38,850 | 23,062 | 5,611 | 3,368 |
| | $10^{-7}$ | 490 | 1,121 | 6,521 | 5,940 | 2,313 | 1,014 | 1,370 |
| REV2 | $10^{-4}$ | 285 | 590 | 1,345 | 9,772 | 4,075 | 1,888 | 2,083 |
| ctrl cen- | $10^{-5}$ | 713 | 294 | 296 | 555 | 9,348 | 12,302 | 5,043 |
| trifuging | $10^{-6}$ | 308 | 351 | 414 | 326 | 3,509 | 1,568 | 653 |
| REV3.1 | $10^{-4}$ | 203 | 582 | 569 | 8,425 | 3,703 | 3,778 | 4,559 |
| exp$^d$ ctrl | $10^{-5}$ | 572 | 505 | 577 | 1,395 | 3,155 | 12,243 | 4,607 |
| 60 min. | $10^{-6}$ | 440 | 339 | 1,165 | 1,250 | 714 | 653 | 994 |
| non-infected cells | | 247 | 258 | 363 | 291 | 630 | 630 | 366 |

*cpm/ml: reverse transcriptase activity (RT) in 1 ml of culture supernatant. The viral production is considered to be positive for a RT activity of more than 5.000 cpm/ml (bolt type numbers)

We note in Table 6 that 14 days after infection, the cells inoculated with dilutions less than or equal to 10-7 of sample REV1 or with the dilution of 10-4 of samples REV2 and REV3.1 have viral particles in the culture supernantants. Under experimental conditions, the strength of the virus is defined as the inverse of the last dilution being 100% infectious. The strengths of the control samples are, respectively, 107 UI/ml for REV1 and 104 for REV2 and REV3.1. A reduction of infectious strength is thus noted for the experimental controls. It is of a logarithmic factor of the order of 3 for the centrifuged sample, and for the control virus left for one hour at room temperature and centrifuged. In FIG. 1, we note that no reverse transcriptase activity is revealed in the culture supernantants inoculated with a $\frac{1}{10}$ dilution of virus samples treated with BKF for 30 or 60 minutes. These results are to be compared to those obtained with control REV3.1 which represents an infectious strength of 104 UI/ml.

Figure 2:
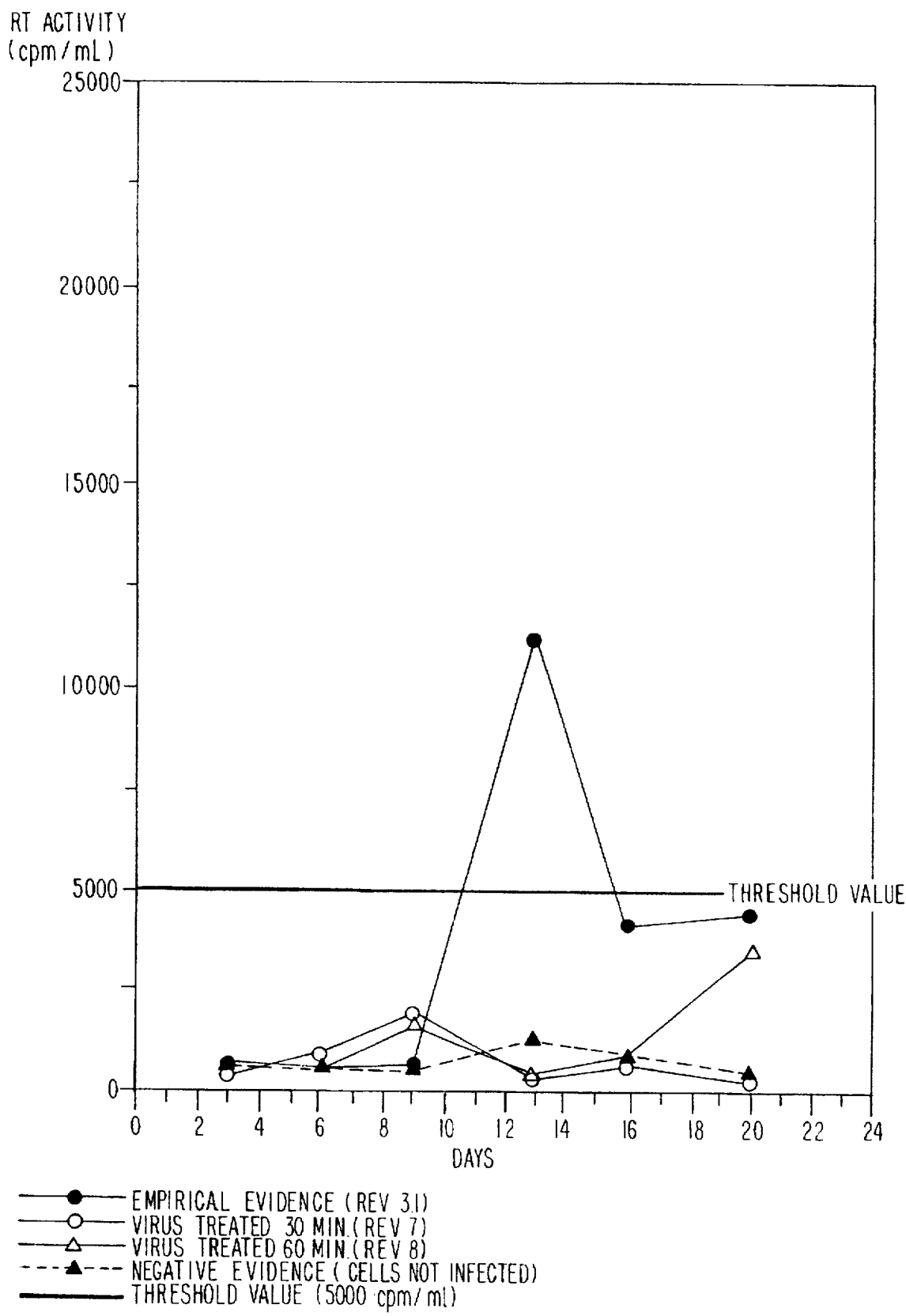

Taking into account these results, a second experiment was carried out by inoculating PBMC lymphocytes with ½ dilution of viral samples treated with BKF in order to confirm the absence of infectious viruses in the samples. The results of RT activity titration in the culture supernatants are represented in FIG. 2. No RT activity was detected, while control virus sample REV3.1 showed positive at dilution 10-5.

Figure 3:
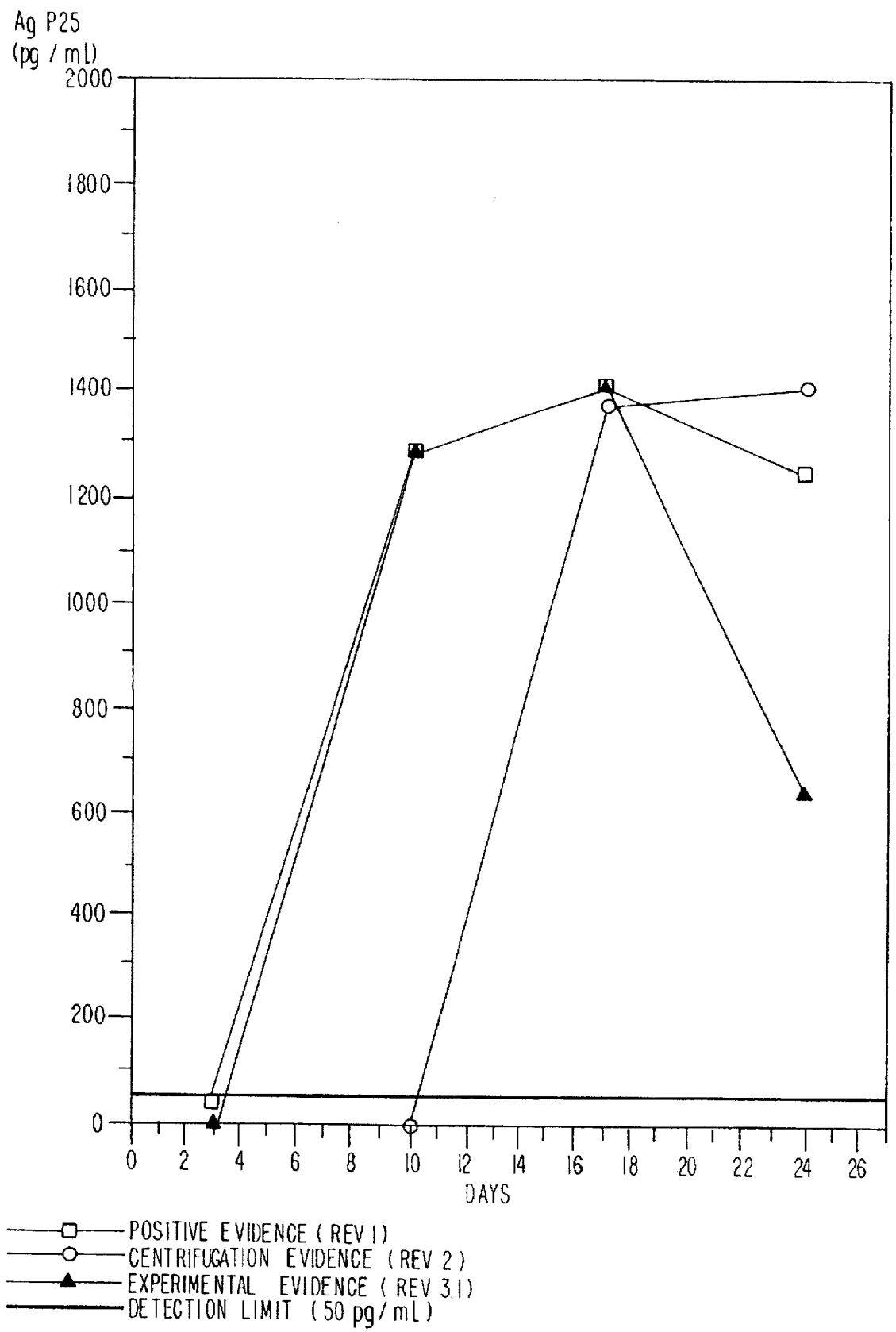

FIG. 3 represents the results of titration of antigen P25 in the control viral samples. The amount of antigen P25 is expressed in pg/ml and is evaluated using standard curve established from a reference antigen solution supplied by the manufacturer. The strengths evaluated 16 days after infection were $10^7$ UI/ml for REV1, $10^5$ UI/ml for REV2 and $10^4$ UI/ml for REV3.1.

Figure 4:
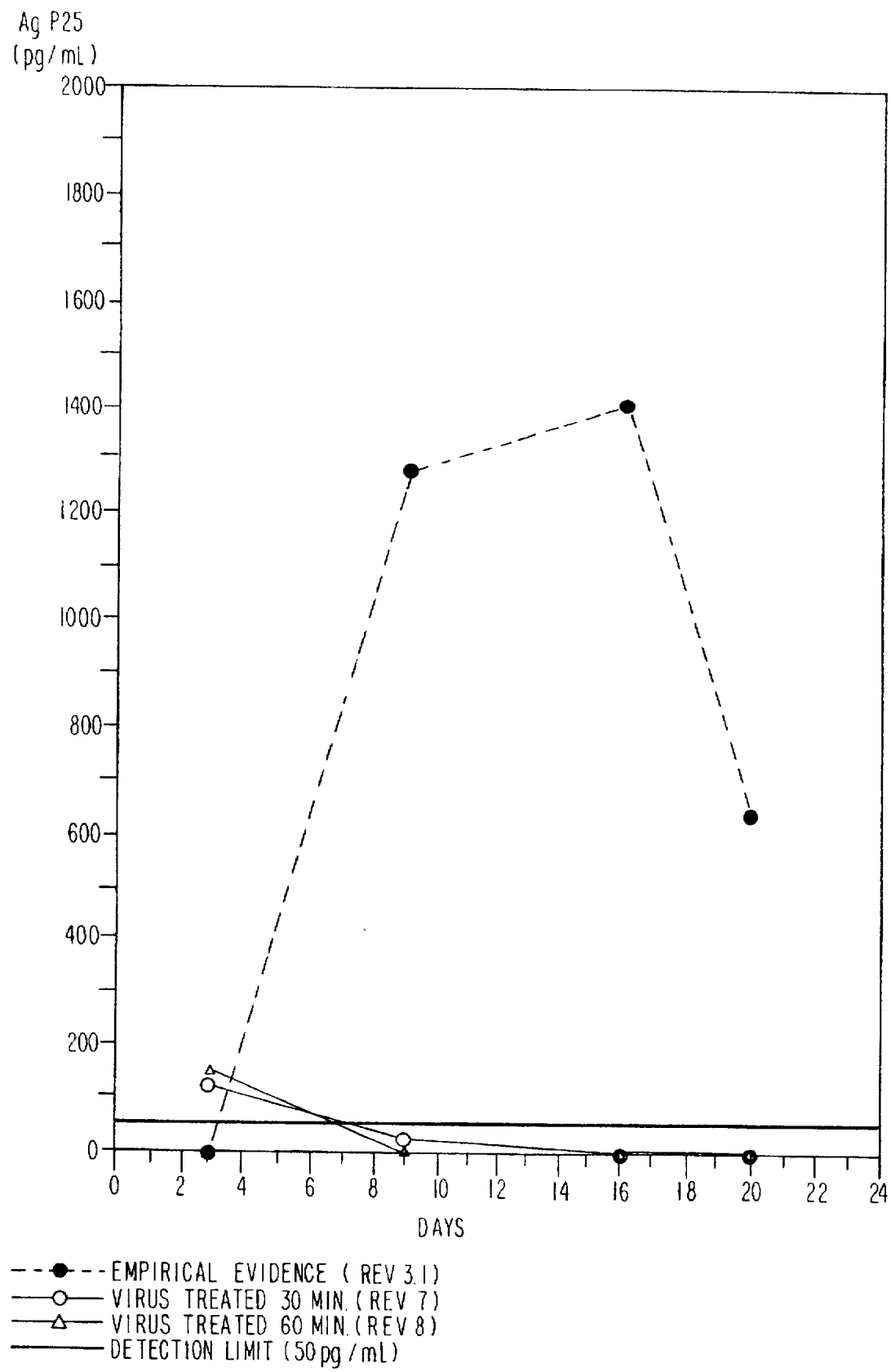

FIG. 4 gives the strength in P25 antigens on the lymphocyte supernatants inoculated with ½ dilutions of viral samples treated with BKF. We note that samples REV7 and REV8 are negative for antigen P25. These results thus confirm those obtained by following the viral expression by reverse transcriptase activity strength in the supernatants of the cultures exposed to treated or untreated virus.

Thus, these trials show that benzalkonium fluoride at 20 μg/ml induces a loss of infectious capacity in the HIV-1 virus in vitro by a logarithmic factor of 5 for activated human lymphocytes. Thus benzalkonium fluoride at 20 μg/ml proves to be a virucide on the AIDS virus in vitro.

Example 3

Local and general tolerance of administration of benzalkonium fluoride intravenously was tested on dogs.

Two beagles, one male and one female, of an initial weight of around 10 kg, 6 months old, in good health, wormed and vaccinated, were placed in an animal house. They were submitted to an intravenous treatment of 2 mg per kg per day of benzalkonium fluoride diluted at 2.10 g/l in an isotonic solute of sterile apyrogenic sodium chloride. The solution was packaged in 10 ml ampoules and 0.95 ml per kg per day was injected rotating the injections on the vein of each leg. The injection was carried out using an epicranian micro-perfuser mounted on a plastic syringe, and the administration was slow intravenous over around 90 seconds. The treatment was given for 28 days. Urine tests were performed before the start of treatment, at the middle (after 14 days) and at the end of the treatment.

Also, blood samples were taken from the jugular before starting treatment, after 14 days and after 28 days of treatment. Haematological examination and complete biochemical titration were carried out on these samples.

At the end of the treatment, the animals were killed, and we proceeded with anatompathological examinations and weighing of the following organs: liver, kidneys, spleen, adrenal, testicles, ovaries, thymus, thyroids. We also proceeded with histological examinations on most of the vital organs.

No modification of sympomatological behaviour was observed following the treatment. During the first two weeks, the injections could be given without difficulty. After, an oedema appeared.

The body weight of the animals remained stable during the entire experimental period. The rectal temperature of the male remained stable and that of the female dog increased 1° C. during the experiment. No notable variation in blood pressure or heart rate was observed. Also, the various electrocardiographic parameters remained stable throughout the entire experimental period.

For the female dog, urine samples showed no signs of haemolysis at the start, in the middle and at the end of treatment. For the male dog, we noted a high level of blood in the urine at the start of treatment. The dog was left in a diuresis cage for 48 hours, after which the urine showed an absence of blood and traces of ketonic bodies, absence of glucose and traces of proteins. The quantities of sodium and potassium showed variations for the male dog but remained almost stable for the female. At the end of treatment, no trace of blood was found in the urine taken from the bladder of the male dog at autopsy time.

Among the haematological parameters, only the number of leukocytes increased after two weeks for the female dog and after four weeks for the male. This increase corresponded to the appearance of oedemas in a leg.

In the biochemical parameters, an increase in alkaline phosphatase and LDH was noted. No other significant variation was noted.

Histological examination of the various organs showed no alteration due to treatment other than local reactions at the injection sites. Also, despite the severity of the treatment, no remarkable toxic effect of benzalkonium fluoride injected intravenously showed up.

Example 4

The high toxicity of benzalkonium fluoride in unique administration in mice and guinea pigs was determined by the Behrens and Karber method, by intracardiac, intravenous and intraperitoneal injection. The animals used were young adult albino mice and albino guinea pigs. Ten animals were used for each dose administered, five males and five females. The benzalkonium fluoride was used in a 3 g/l isotonic solution of sterile apyrogenic sodium chloride. We observed the animals for 7 days after unique administration carried out using a sterile needle adapted to a syringe graduated in 1/10 ml to allow the treatment of each animal with an exact dose. The animals were weighed each day during the observation period.

The LD 50 (lethal dose 50) was determined. The results are given in Table 7.

TABLE 7

| LD 50 (mg/ml) | intravenous | intraperi-toneal | intracardiac |
|---|---|---|---|
| Male mouse | 33.24 | 33.10 | — |
| Female mouse | 36.60 | 34.60 | — |
| Male guinea pig | — | 28.50 | 15.50 |
| Female guinea pig | — | 20.50 | 16.50 |

Thus we note that benzalkonium fluoride by intravenous, intraperitoneal or intracardiac injection has a sufficiently low toxicity for us to envisage its administration by intravascular injection at doses where it is nevertheless active, particularly at 20 to 23 mg/l of blood of the patient to be treated.

Example 5

In vivo trials were carried out on dogs suffering from parvovirus. These dogs were treated with slow perfusion of benzalkonium fluoride C14 dissolved at 2.1 g/l in an isotonic solute of sterile apyrogenic sodium chloride.

A male German Shepherd weighing 20 kg, eight months old, suffering from parvovirus (gastro-enteritis with dehydration, sero-hæmorragic enteritis with high urea level) was treated with two injections at a 12 hour interval with two 10 ml ampoules. 6 days after the start of treatment we noted both excellent tolerance and recovery of the dog.

A female German Shepherd aged 7 months and weighing 10 kg, suffering from parvovirus for 4 days (gastro- enteritis with dehydration, sub-comatose state, hæmoconcentration, high urea level, hæmorragic salt) was treated with two injections separated by 12 hours of the solution according to the invention. The first injection was 10 ml and the second 20 ml. A general associated treatment was given for 8 days. Tolerance to the treatment proved to be excellent and we noted total recovery after 20 days.

A male Newfoundland of 6 months and weighing 28 kg suffering from parvovirus was also treated with two slow intravenous injections of 10 ml separated by 12 hours. At the end of the second day, the blood had disappeared from the urine and the dog no longer vomited. After four days, the animal was eating normally. On the 18th day, total recovery was noted.

A female Rottweiler aged 4 months and weighing 15 kg suffering from parvovirus was also treated in the same way. Complete recovery was noted after 18 days.

The same treatment was applied to a female German Pointer of 2 months and weighing 12 kg. The same recovery was noted (normal eating after 4 days and total recovery confirmed after 18 days).

Three puppies (4 month male of 12 kg, 4 month male of 7 kg and 2 month female of 6 kg) suffering from violent evolutive gastro-enteritis were also treated with two slow intravenous injections at 12 hours interval. The puppies were suffering from sero-hæmorragic gastro-enteritis. Death occurred within two days.

Thus, apart from the three failures obtained on the very young animals suffering from severe symptoms, the invention allowed treatment of parvovirus in dogs.

Example 6

The invention was used to treat dogs suffering from Carré's disease. This disease, considered fatal and without treatment, is due to an ultravirus.

Twelve dogs were treated with one 10 ml ampoule of benzalkonium fluoride solution at 2.1 g/l for 20 kg of animal. The injection was given once per day for three days. The dogs also had associated treatment (vitamins, antibiotics, vaccines, etc.).

The treatment proved effective for seven dogs who were saved and for whom total recovery was noted after 18 days.

Among the seven dogs cured, five came from a pack in which there had already been two deaths, and which was greatly affected by the disease. They had already undergone an ineffective treatment. The symptoms were mainly purulent nasal mucous, cough, diarrhoea, suppurating conjunctivitis and fever of between 40° C. and 40.5° C. average. The efficacy of the treatment was thus particularly surprising.

The five other dogs treated all presented nervous symptoms (generalised trembling) and could not be treated. Consequently, the invention allowed treatment of the cases of Carré's disease not accompanied by nervous manifestations.

Example 7

We determined the hæmolytic concentration of benzalkonium fluoride on total human, guinea pig and rabbit blood in vitro.

This experiment was carried out with a hospital method for looking for peripheral anæmia. We used dilutions of a benzalkonium fluoride solution at 3 per 1000: 300 mg/L, 150 mg/L and 75 mg/l in an isotonic solute of sterile apyrogenic sodium chloride. Each of the three dilutions was mixed at equal volume with the blood of the three species (man, guinea pig and rabbit). The mixture was slowly shaken for 5 minutes thirty then centrifuged for three minutes at 3,500 rev/min. Hæmolysis was shown by a more or less dark red colouring of the persistent plasmatic supernatant. The real concentrations tested were thus 150 ppm, 75 ppm and 35.5 ppm of benzalkonium fluoride. Each test was doubled.

Not having noted hæmolysis at 37.5 mg/l, new tests were carried out on six samples of human blood, under the same conditions, at 20 mg/L and 35 mg/l of benzalkonium fluoride.

Table 8, below, gives the results obtained.

TABLE 8

| | Concentration of benzalkonium fluoride (in ppm or mg/l) 6 samples | | | | |
|---|---|---|---|---|---|
| | 150 | 75 | 37.5 | 35 | 20 |
| GUINEA PIG | +++ | + | 0 | — | — |
| RABBIT | +++ | + | 0 | — | — |
| MAN | ++ | + | 0 | 0 | 0 |

+ to +++: degree of red colouring due to haemolysis

Thus benzalkonium fluoride at a concentration equal to or less than 20 mg/l does not provoke haemolysis in human blood, and this with a wide margin of security.

According to the invention, we may nevertheless easily check the haemolytic concentration of benzalkonium fluoride on the blood of the patient to be treated before injection.

Example 8

We treated patients suffering from AIDS in the evolutive or terminal phase with a solution consisting of 2.1 g/l of benzalkonium fluoride. Before injection, the haemolytic concentration of benzalkonium fluoride was determined and we verified that it was well above that of the solution used.

A male of 37 years, weighing 70 kg, presented the following symptoms: asthenia, weight loss, bucal candidiasis, fever with a plateau of 39.7° C., ELISA (enzyme linked immunosorbant assay) test and WESTERN BLOT (confirmation test) positive, number of $CD_4$ (receptors at the surface of T lymphocytes responsible for regulation of the immune response) less than 200 (the normal value being of the order of 1,000). The patient was treated with slow intravenous injections of 50 ml of benzalkonium fluoride $C_{14}$ at 2.1 g/l repeated every twelve hours in cures of three days separated by five days of observation. Despite pain at the injection point which appeared at the end of the second cure, observation at one month and seven months after treatment showed a good general state of the patient who could take up his professional activity. The number of $CD_4$ had risen to 600.

A male of 28 years, weighing 57 kg, presented the following symptoms: asthenia, weight loss, vomiting, diarrhoea, bucal candidiasis, fever with a plateau of 39.5° C., totally beddriden patient ELISA and WESTERN BLOT tests positive, number of $CD_4$ equal to 20. This patient underwent two cures of three days as described above. On the tenth day after the start of treatment, we noted a clear improvement in the general state, disappearance of the fever, vomiting and diarrhoea and weight gain (59.6 kg). The patient could get up and walk.

A male of 44 years, weighing 78 kg, presented the following symptoms: asthenia, anorexia, insomnia, fever with a plateau of 39.7° C., ELISA and WESTERN BLOT tests positive, number of $CD_4$ at 650. The patient was treated with slow intravenous injections of 50 ml of benzalkonium fluoride $C_{14}$ at 2.1 g/l repeated every eight hours for three days with a complementary antibiotic treatment (based on Doxycycline) of two capsules each evening.

On the sixth day after the start of treatment, the fever had disappeared. Two months after the start of treatment, we noted a progressive disappearance of the asthenia. At the fourth month, the patient had returned to a normal general state and taken up his military activity.

A male of 42 years, weighing 52 kg, presented the following symptoms: asthenia, anorexia, sweating, inguinal adenopathy, diarrhoea, cephalagia, bucal candidiasis, fever with a plateau of 39° C., ELISA and WESTERN BLOT tests positive, number of $CD_4$ at 200. The patient was treated with a cure of three days of slow intravenous injections of benzalkonium fluoride $C_{14}$ at 2.1 g/l every twelve hours. On the third day, a clear fall in the fever was noted. Three and a half months after the start of treatment, the patient presented a good general state, a weight of 56 kg, the number of $CD_4$ had risen to 700 and there were no clinical symptoms.

Example 9

We determined the activity in vitro of benzalkonium fluoride on the mycobacterium tuberculosis (wild strain).

This experiment was carried out with the BOWEIN-STEIN JENSEN medium surface impregnation method. The quantity of active substance absorbed by the medium is expressed in $cm^2$.

The volume of the appropriate dilution of benzalkonium fluoride was 0.25 ml per tube of medium in order to arrive at concentrations of benzalkonium fluoride of 0.1, 0.2 and 0.3% per $cm^2$ surface of BOWEINSTEIN JENSEN medium.

A control tube, without benzalkonium fluoride, was used for each of the series.

Three series of tests were carried out with dilutions of 0.1, 0.01 and 0.001 of the mother solution of the Bacterium Tuberculosis strain prepared at 1 mg/ml.

All the tests were carried out in double.

After four weeks of incubation at 37° C., the results showed an inhibition of the culture with concentrations of benzalkonium fluoride of 0.1, 0.2 and 0.3% per $cm^2$ surface of BOWEINSTEIN JENSEN medium, and this was observed for the three dilutions at 0.1, 0.01 and 0.001 of the Bacterium Tuberculosis mother culture.

Table 9, below, gives the results obtained.

TABLE 9

| | BK 0.1 | BK 0.1 | BK 0.01 | BK 0.01 | BK 0.001 | BK 0.001 |
|---|---|---|---|---|---|---|
| CONTROL | (+++) | (+++) | (+++) | (+++) | (+++) | (+++) |
| BKF 0.1%/cm² | (−) | (−) | (−) | (−) | (−) | (−) |
| BKF 0.2%/cm² | (−) | (−) | (−) | (−) | (−) | (−) |
| BKF 0.3%/cm² | (−) | (−) | (−) | (−) | (−) | (−) |

(+++) = positive culture
(−) = negative culture

We claim:

1. Solution administrable by intravascular injection in a human or an animal which comprises an effective amount up to 0.23% by weight of a benzalkonium fluoride having the formula:

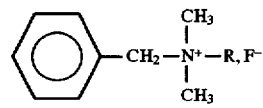

where R is an alkyl radical which may vary between $C_8H_{17}$ and $C_{18}H_{37}$, dissolved in an excipient injectable intravascularly.

2. Solution according to claim 1, which comprises about 0.2% by weight of benzalkonium fluoride.

3. Solution according to claim 1, which contains at least about 0.05% by weight of benzalkonium fluoride.

4. Solution according to claim 1, wherein R is between $C_{12}H_{25}$ and $C_{14}H_{29}$.

5. Solution according to claim 1, wherein R is $C_{14}H_{29}$.

6. Solution according to claim 1, packaged in 5 to 15 ml ampoules, containing between 0.5 and 23 mg of benzalkonium fluoride.

7. Solution according to claim 1, packaged in 10 ml ampoules, containing about 21 mg of benzalkonium fluoride.

8. Solution according to claim 1, which consists of benzalkonium fluoride dissolved in a physiological solvent.

9. Solution according to claim 1, which further contains at least one metallic derivative of fluorine.

10. Solution according to claim 9, wherein said derivative is lithium fluoride.

11. Method of treatment of viral or infectious diseases in a human or an animal, which comprises administering by intravascular injection a solution of at least one benzalkonium fluoride of the formula:

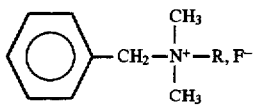

where R is an alkyl radical which may vary between $C_8H_{17}$ and $C_{18}H_{37}$, dissolved at an effective concentration of up to 0.23% by weight in an excipient injectable intravascularly, wherein the disease is induced by picornavirus, adenovirus, herpetovirus, HIV virus, parvovirus or is Carré's disease.

12. Method according to claim 11, wherein said solution is an intravascular injection solution comprising about 0.2% by weight of benzalkonium fluoride.

13. Method according to claim 11, wherein the intravascular injection solution comprises more than 0.005% by weight of benzalkonium fluoride.

14. Method according to claim 11, wherein the concentration of benzalkonium fluoride administered by intravascular injection is delivered by slow injection of 0.5 to 23 mg of benzalkonium fluoride per liter of blood of the patient treated.

15. Method according to claim 11, wherein the concentration of benzalkonium fluoride administered by intravascular injection is delivered by slow injection of 21 mg of benzalkonium fluoride per liter of blood of the patient treated.

16. Method according to claim 11, wherein R is between $C_{12}H_{25}$ and $C_{14}H_{29}$.

17. Method according to claim 11, wherein the intravascular injectable solution comprises between 0.5 to 23 mg of benzalkonium fluoride dissolved in between 5 and 15 ml of solvent.

18. Method according to claim 11, wherein the intravascular injectable solution comprises 21 mg of benzalkonium fluoride dissolved in 10 ml of solvent.

19. Method according to claim 11, wherein the intravascular injectable solution comprises benzalkonium fluoride dissolved in a physiological solvent.

20. Method according to claim 11, wherein the intravascular injectable solution comprises at least one metallic fluorine derivative.

21. Method according to claim 20, wherein said derivative is lithium fluoride.

22. Method of treatment of AIDS in the declared or evolutive phase, which comprises administering to a human suffering from AIDS in the declared or evolutive phase by intravascular injection a solution of at least one benzalkonium fluoride of the formula:

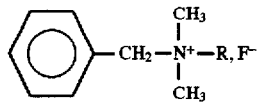

where R is an alkyl radical which may vary between $C_8H_{17}$ and $C_{18}H_{37}$ dissolved at an effective concentration of up to 0.23% by weight in an excipient injectable intravascularly.

23. Method of treatment of tuberculosis, which comprises administering to a human suffering from tuberculosis by intravascular injection a solution of at least one benzalkonium fluoride of the formula:

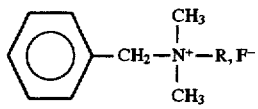

where R is an alkyl radical which may vary between $C_8H_{17}$ and $C_{18}H_{37}$, dissolved at an effective concentration of up to 0.23% by weight in an excipient injectable intravascularly.

* * * * *